United States Patent [19]

Shaw et al.

[11] Patent Number: 5,559,271

[45] Date of Patent: Sep. 24, 1996

[54] ORGANIC POLYSULFIDE COMPOSITIONS HAVING REDUCED ODOR

[75] Inventors: James E. Shaw; Howard F. Efner, both of Bartlesville, Okla.

[73] Assignee: Phillips Petroleum Company, Bartlesville, Okla.

[21] Appl. No.: 508,150

[22] Filed: Jul. 26, 1995

[51] Int. Cl.$^6$ ............. C07C 319/28; C07C 319/26; C07C 319/22

[52] U.S. Cl. ................. 568/21; 568/25

[58] Field of Search ............... 568/21, 25

[56] References Cited

U.S. PATENT DOCUMENTS

| | | | |
|---|---|---|---|
| 2,571,157 | 10/1951 | Olin | 260/609 |
| 2,794,769 | 6/1957 | Jezl | 196/32 |
| 2,862,804 | 12/1958 | Petty | 44/76 |
| 3,308,166 | 3/1967 | Biensan et al. | 260/608 |
| 3,730,850 | 5/1973 | Louthan | 568/21 X |
| 4,355,183 | 10/1982 | Nash et al. | 568/21 X |
| 4,876,389 | 10/1989 | Gongora et al. | 568/26 |
| 5,218,147 | 6/1993 | Shaw | 568/21 |
| 5,403,961 | 4/1995 | Shaw | 568/21 |

FOREIGN PATENT DOCUMENTS 58-140063  8/1983  Japan .

*Primary Examiner*—Paul F. Shaver
*Attorney, Agent, or Firm*—Lucas K. Shay

[57] ABSTRACT

A composition which comprises a major amount of an organic polysulfide and an odor-masking amount of an odor-masking compound selected from the group consisting of wintergreen, cinnamons, vanillins, terpenes, sesquiterpenes, and combinations of any two or more thereof is provided wherein the composition has a more pleasant odor than the organic polysulfide.

19 Claims, No Drawings

ORGANIC POLYSULFIDE COMPOSITIONS HAVING REDUCED ODOR

FIELD OF THE INVENTION

The present invention relates to masking the odor of organic polysulfides and to organic polysulfide compositions having reduced or more pleasant odor than organic polysulfides.

BACKGROUND OF THE INVENTION

Organic polysulfides and particularly dialkyl polysulfides such as tri-, tetra-, and penta-sulfides have been found useful for many purposes such as additives for elastomers, antioxidants for lubricating oils, intermediates for the production of organic chemicals, insecticides, germicides and as an additive to diesel fuels to improve the octane number and ignition qualities of these fuels. These polysulfides have also been found useful in the compounding of extreme pressure lubricants and in the acceleration of rubber treating processes. Because of the high sulfur content, organic polysulfide compounds are also useful in presulfiding catalysts used in refinery processes.

Such organic polysulfide compounds can be prepared by reacting mercaptans with elemental sulfur in the presence of a basic catalyst. For example, Biensan et al (U.S. Pat. No. 3,308,166) discloses that organic polysulfides can be prepared from a mercaptan and sulfur catalyzed by an amine using an alcohol promoter.

A conventional process for producing an organic polysulfide compound such as di-t-dodecyl polysulfide is to react a mercaptan such as t-dodecylmercaptan with elemental sulfur in the presence of triethylamine as catalyst. However, the organic polysulfide thus prepared is associated with some unreacted mercaptans and residual $H_2S$ contributing to a very unpleasant odor. Additionally, possibly because of the unreacted mercaptans and the amine catalyst, the product always becomes very unstable, i.e., the product turns cloudy, probably due to degradation of the organic polysulfide causing precipitation of sulfur. The instability along with the unpleasant odor greatly reduce the desirability and utility of the organic polysulfide.

There is therefore a need to substantially reduce the odor associated with an organic polysulfide compound. Kamii et al (Japanese Application 58-140,063) discloses a process for deodorizing dialkyl polysulfides by contacting a polysulfide-bearing fluid with 1,2-epoxy compounds. The 1,2-epoxy compounds apparently react directly with the unreacted mercaptan and hydrogen sulfide, thereby producing a product with reduced odor. Excess 1,2-epoxy compounds are reportedly removed by conventional methods, such as vacuum distillation.

However, the process disclosed in Kamii et al requires vigorous and extensive chemical reaction. Additionally, the process disclosed in Kamii et al produces a product that still has such a high mercaptan sulfur level that it would contribute to the instability of the organic polysulfide product. Furthermore, even after vigorous chemical treatment, the unpleasant odor, through reduced, still is associated with the treated organic polysulfide.

It would therefore be a significant contribution to the art to develop a organic polysulfide composition whose unpleasant odor is substantially masked or reduced and a process for the deodorization or masking of an organic polysulfide so that the organic polysulfide is made more useful for industrial uses.

SUMMARY OF THE INVENTION

An object of the present invention is to develop an organic polysulfide composition whose unpleasant or objectionable odor is substantially reduced, hidden, or masked. Another object of the present invention is to provide a process for substantially masking the odor associated with organic polysulfide compounds. Still another object of the present invention is to provide a process for preparing an organic polysulfide composition having its unpleasant or objectionable odor substantially masked.

An advantage of the present invention is the substantial masking of the unpleasant odor of an organic polysulfide compound without subjecting the polysulfide to chemical reactions. Other advantages, objects, and features will become more apparent as the invention is more fully disclosed in the following disclosure and claims.

According to an embodiment of the present invention, an organic polysulfide composition having a more pleasant odor than an organic polysulfide compound is provided which comprises a major amount of an organic polysulfide compound and an odor-masking amount of an odor-masking compound.

According to another embodiment of the invention it is provided a process for substantially masking the unpleasant odor of an organic polysulfide compound which comprises contacting the organic polysulfide compound with an odor-masking amount of an odor-masking compound.

DETAILED DESCRIPTION OF THE INVENTION

According to the present invention, any organic polysulfide compounds can be used in producing the organic polysulfide compositions in the present invention. Preferably, the organic polysulfide has a general formula of $RS_nR'$ wherein R and R' can be the same or different and are each selected from alkyl radicals, aryl radicals, alkaryl radicals, aralkyl radicals, and combinations of any two or more thereof. Each R or R' can have about 1 to about 30, preferably 1 to about 20, and more preferably 1 to 15 carbon atoms. The subscript n is a number of 2 to about 10. Most preferably R and R' are each alkyl radicals having 3 to 15 carbon atoms and n is 3 to about 8. Even more preferably, R and R' are alkyl radicals having 9 to 12 carbon atoms and n is 3 to 6. Examples of the presently preferred organic polysulfides include, but are not limited to, di-t-butyl trisulfide, di-t-nonyl polysulfide, di-t-dodecyl polysulfide, di-t-butyl polysulfide, di-t-dodecyl trisulfide, di-t-nonyl trisulfide, and combinations of any two or more thereof.

The organic polysulfide can be prepared by the reaction of mercaptans and elemental sulfur catalyzed by a basic catalyst. The reaction is depicted as $RSH+R'SH+(n-1)S \rightarrow RS_nR'+H_2S$ where R, R' and n are the same as those described above. The reaction can be carried out under any suitable reaction condition, in any suitable reaction vessel, so long as an organic polysulfide can be produced. The basic catalyst can be a metal hydroxide such as sodium hydroxide, a metal oxide or a metal salt such as MgO and $Na_2CO_3$, and an amine such as triethylamine. Generally, one of the reactants, either the mercaptan or sulfur, is slowly added to the other reactant in the presence of a basic catalyst. The sulfur, upon addition, readily dissolves in the solution. Mixing of the solution and/or operating at higher than ambient temperatures will enhance the reaction rate. The amount of sulfur added depends on the desired sulfur content of the polysulfide product. For an average sulfur content of n-sulfurs per polysulfide molecule, (n−1) moles of sulfur is added and 1 mole of hydrogen sulfide is released per 2 moles of mercaptans reacted. The weight of the basic catalyst as a percentage of the weight of mercaptan can be in the range of 0.05 to 5%, preferably 0.1 to 2.0%, and most preferably 0.2 to 1.0%.

Following completion of the reaction, residual hydrogen sulfide may be removed from the organic polysulfide by either an inert gas purge or by vacuum stripping. When using an inert gas purge, the preferred gases are nitrogen, air, or combinations thereof.

Following the removal of residual hydrogen sulfide, the organic polysulfide can be contacted with an alkylene oxide and a basic inorganic catalyst in a solvent as disclosed in U.S. Pat. No. 5,218,147, disclosure of which is herein incorporated by reference. The odor of the organic polysulfide can also be first reduced by any other means known to one skilled in the art.

An organic polysulfide, with or without treatment with an alkylene oxide, can be combined with an odor-masking amount of an odor-masking compound to produce the organic polysulfide compound of the present invention. The odor-masking compound can be any chemical compound that is capable of masking the unpleasant odor of an organic polysulfide. Generally, the odor-masking compounds can be selected from the group consisting of cinnamons, wintergreen (methyl salicylate), terpenes, sesquiterpenes,, vanillins and combinations of any two or more thereof. Examples of suitable vanillins include, but are not limited to, vanillin (4-hydroxy-3-methoxybenzaldehyde), ethyl vanillin (3-ethoxy-4-hydroxybenzaldehyde), o-vanillin (3-methoxysalicylaldehyde), vanillic acid (4-hydroxy-3-methoxybenzoic acid), oleoresin vanillin, and combinations of any two or more thereof. According to the present invention, limonene is not a preferred or desirable terpene. Examples of suitable terpenes include, but are not limited to, menthol, piperitone, menthyl acetate, neomenthol, pulegone, spearmint ((−)-carvone), carvyl acetates, cornmint, scotch mint, peppermint, α-pinene, β-pinene, linalool, nerol, α-terpinene, menthofuran, β-terpinene, Y-terpinene, myrcene, geraniol, geranial, neral, citronellal, menthone, isomenthone, 1,8-cineole, ascaridole, bornneol flavonone, terpinolene, sabinene, camphene, citronellol, and combinations of any two or more thereof. Examples of suitable cinnamons include, but are not limited to, cinnamic aldehyde, cinnamic alcohols, cinnamic acids, methyl cinnamate, benzyl cinnamate, cinnamyl acetate, cinnamyl cinnamate (styracin), and combinations of any two or more thereof. These compounds are commercially available. The presently preferred odor-masking compounds are vanillin and derivatives thereof. The presently most preferred odor-masking compounds are vanillin and ethyl vanillin.

As disclosed above, the amount required to prepare an organic polysulfide compound having its unpleasant odor substantially masked is an odor-masking amount that is sufficient to effect a substantial reduction or masking of the unpleasant odor of an organic polysulfide compound. The amount can generally be in the range of from about 1 to about 10,000, preferably about 20 to about 5,000, and most preferably from 50 to 1,000 mg of an odor-masking compound per Kg of organic polysulfide. The term "major amount" used in the present invention denotes an amount or concentration of at least 75 weight percent (%), preferably at least 90%, and most preferably at least 95%.

The composition of the present invention can be carried out by simply combining an odor-masking compound with an organic polysulfide. According to another embodiment of the present invention, the combining can be carried out by addition of an odor-masking compound to an organic polysulfide, or vise versa, followed by heating, mixing, or both, if desired. Any mixing means or methods known to one skilled in the art can be used. The process can be carried out under any conditions. Presently, it is preferred that the process be ,carried out under about atmospheric pressure and at a temperature in the range of from about 10° C. to about 100° C., preferably about 20° C. to about 100° C., and most preferably 20° C. to 80° C. The time period required for producing an organic polysulfide composition of the present invention is the time that is sufficient to effect the production of an organic polysulfide composition having a more pleasant odor.

The process of the second embodiment of the present invention can be carried out in any suitable vessel. It is preferred to carry out in the same vessel where the crude organic polysulfide is prepared.

The process of the invention can also be carried out continuously. For example, the combining of a terpene or vanillin with the organic polysulfide can be done by employing continuous stirred tank reactors connected in series, packed columns or towers, and other continuous flows that are readily within the realm of one skilled in the art.

The following examples are provided to further illustrate the practice of the invention and are not intended to limit the scope of the invention or the claims.

EXAMPLE I

This example illustrates the prepared of di-t-nonyl polysulfide having an average of 5 sulfurs per molecule.

T a 1 liter autoclave reactor which had been flushed with nitrogen ($N_2$), it was added a solution of 599 g (3.74 mole) t-nonyl mercaptan and 3.8 g (0.037 mole) triethylamine. The autoclave was heated to 30° C. and the contents were stirred rapidly (1000 rpm). Sulfur (240 g, 7.49 mole) in a 300 ml stainless steel bomb equipped with an internal thermocouple was melted by heating at 120°–135° C. under $N_2$. With the melted sulfur at 135° C., the $N_2$ pressure above the sulfur in the bomb was increased to 200 psi, and the valve and tubing between the bomb and autoclave were heated so sulfur would not solidify in them during the sulfur transfer. The liquid sulfur was added over a 2 minute time period so as to avoid solidification of sulfur in the tube that went through the autoclave body. The addition of the liquid sulfur over a 2 minute time period caused the autoclave temperature to increase from 30° C. to the desired process temperature of 45° C.

When the sulfur addition was completed, the autoclave pressure had increased to 150 psi due to $H_2S$ evolution. The autoclave pressure was then decreased to 60 psi by the controlled venting of $H_2S$ for about 0.5 hour. At this point, $H_2S$ was removed by pressurizing the autoclave with $N_2$ to 100 psi and then venting to 60 psi. This was repeated 3 more times over a 0.5 hour time period and the pressure (mainly due to $N_2$) was allowed to decrease near atmospheric whereupon the system was opened to a vent line. Heating to 45° C. with rapid stinting (1000 rpm) was continued for an additional 1.5 hours (total time after addition of all sulfur was 2.5 hours). Nitrogen was then bubbled at 2 SCFH (standard cubic feet per hour) through the reaction mixture at 45° C. with rapid stirring (1000 rpm) for 4 hours to remove most hydrogen sulfide and triethylamine.

To 775 g of the crude di-t-nonyl polysulfide prepared by the above process was added 4.45 g of a solution of 20% NaOH in methanol except where it is noted in Table I. The mixture was heated with stirring to 70°–72° C. and 13.3 g of propylene oxide was added over 15 minutes. The mixture was heated with stirring for an additional 2.25 hours at 70°–72° C. Then the stirred mixture was sparged with nitrogen (approximately 2 SCFH) at 70°–72° C. for 1.5 hours. This removed methanol and unreacted propylene oxide. After cooling, the mixture was filtered to give 775 g (1000% yield) of clear yellow di-t-nonyl polysulfide.

EXAMPLE II

This example illustrates the preparation of an organic polysulfide compound whose unpleasant odor was substantially masked.

To a glass jar was added 150 g of di-t-nonyl polysulfide obtained in Example I and 0.04 g of vanillin (4-hydroxy-3-methoxybenzaldehyde), and the mixture was mixed well at room temperature (about 25° C.). The vanillin slowly dissolved and only completely dissolved after about 2 days (the vanillin could have been dissolved in an hour at higher temperatures).

Eight people compared the odor from the above jar with that from an identical jar containing only 150 g di-t-nonyl polysulfide and no vanillin. Seven people liked the odor of the jar containing vanillin much better, and one person said both jars were about the same. The seven people said the odor was pleasant but not all could identify it as a vanilla odor.

After more than 2 months the vanilla odor was still present. The vanilla did not change the appearance of the polysulfide. After more than 2 months the polysulfide was still clear with no precipitate.

EXAMPLE III

This example illustrates the preparation of an organic polysulfide using a vanillin derivative wherein the organic sulfide compound had its unpleasant odor substantially masked.

To a glass jar was added 150 g of di-t-nonyl polysulfide and 0.02 g of ethyl vanillin (3-ethoxy-4-hydroxybenzaldehyde) and this was mixed well at room temperature. It took a day to dissolve completely but this would be much faster at a higher temperature.

Four people compared the above with the original di-t-nonyl polysulfide. All four liked the vanillin solution better than the original. At the lower concentration used here than in Example II, most did not notice the vanilla fragrance as much but did notice that the odor of the original polysulfide was masked by the ethyl vanillin.

EXAMPLE IV

This example shows the preparation of an organic polysulfide compound employing another vanillin derivative.

The run was carried out the same as that in Example II except that 0.02 g of o-vanillin (3-methoxysalicylaldehyde or 2-hydroxy-3-methoxybenzaldehyde) was used. Four people compared the resulting polysulfide with the original polysulfide. All said it was not as good as vanillin (Example II) or ethyl vanillin (Example III), although 3 out of 4 liked it better than the original polysulfide.

EXAMPLE V

This example illustrates the preparation of a polysulfide which does not have a reduced odor.

One hundred fifty grams of di-t-nonyl polysulfide and 0.04 g of d-limonene were added to a jar. After mixing well, the odor of this jar was compared with the odor of a jar containing only 150 g of the polysulfide by 4 people. All four people felt the original was better than the one with the limonene. They all had a strong opinion that limonene made the odor worse.

EXAMPLE VI

The run was carried out the same as that in Example V except that 0.04 g of methyl salicylate (oil of wintergreen odor) was used. Four people said the resulting polysulfide composition was not as good as vanillin (Example II) but better than limonene. The odor was marginally better than that of the original polysulfide.

EXAMPLE VII

The run was carried out the same as that in Example V except that 0.08 g peppermint extract. The resulting polysulfide composition seemed to improve odor but only marginal improvement and was not nearly as good as vanillin shown in Example I.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A composition comprising an organic polysulfide and an odor-masking amount of an odor-masking compound selected from the group consisting of wintergreen, terpenes, vanillins, cinnamons, sesquiterpenes, and combinations of any two or more thereof.

2. A composition according to claim 1 wherein said polysulfide has the formula of $RS_nR'$ wherein R and R' are the same or different hydrocarbyl radicals having about 1 to about 30 carbon atoms, and n is a number of 2 to about 10.

3. A composition according to claim 2 wherein said R and R' each has 3 to 15 carbon atoms and n is 3 to 8.

4. A process according to claim 1 wherein said polysulfide is selected from the group consisting of di-t-butyl trisulfide, di-t-dodecyl trisulfide, di-t-dodecyl polysulfide, di-t-nonyl polysulfide, di-t-nonyl trisulfide, and combinations of any two or more thereof.

5. A composition according to claim 1 wherein said polysulfide is di-t-nonyl polysulfide.

6. A composition according to claim 1 wherein said odor-masking compound is selected from the group consisting of wintergreen, vanillin, ethyl vanillin, o-vanillin, vanillic acid, oleoresin vanillin, menthol, piperitone, menthyl acetate, neomenthol, pulegone, spearmint ((−)-carvone), carvyl acetates,, cornmint, scotch mint, peppermint, α-pinene, β-pinene, linalool, nerol, α-terpinene, menthofuran, β-terpinene, Y-terpinene, myrcene, geraniol, geranial, neral, citronellal, menthone, isomenthone, 1,8-cineole, ascaridole, bomneol flavonone, terpinolene, sabinene, camphene, citronellol, cinnamic aldehyde, cinnamic alcohols, cinnamic acids, methyl cinnamate, benzyl cinnamate, cinnamyl acetate, cinnamyl cinnamate (styracin), and combinations of any two or more thereof.

7. A composition according to claim 1 wherein said odor-masking compound is selected from the group consisting of vanillin (4-hydroxy-3-methoxybenzaldehyde), ethyl vanillin (3-ethoxy-4-hydroxybenzaldehyde), and combinations thereof.

8. A composition according to claim 1 wherein said odor-masking compound is present in said composition in the range of from about 1 to about 10,000 mg per Kg of said organic polysulfide.

9. A composition according to claim 1 wherein said odor-masking compound is present in said composition in the range of from about 20 to about 5,000 mg per Kg of said organic polysulfide.

10. A composition comprises a major amount of an organic polysulfide and about 1 to about 10,000 mg of an odor-masking compound per Kg of said organic polysulfide wherein said organic polysulfide has the formula of $RS_nR'$ in which R and R' are each independently a hydrocarbyl radical having 1 to about 30 carbon atoms and n is a number from 2 to about 10; and said odor-masking compound is selected from the group consisting of wintergreen, terpenes, sesquiterpenes, vanillins, cinnamons, and combinations of any two or more thereof.

11. A composition according to claim 10 wherein:

said odor-masking compound is present in said composition in the range of from 50 to 1,000 mg per Kg of said organic polysulfide;

said organic polysulfide is selected from the group consisting of di-t-butyl trisulfide, di-t-butyl polysulfide, di-t-nonyl polysulfide, di-t-dodecyl polysulfide, di-t-nonyl trisulfide, di-t-dodecyl trisulfide, and combinations of any two or more thereof; and said odor-masking compound is selected from the group consisting of wintergreen, vanillin, ethyl vanillin, o-vanillin, vanillic acid, oleoresin vanillin, menthol, piperitone, menthyl acetate, neomenthol, pulegone, spearmint ((−)-carvone), carvyl acetates, commint, scotch mint, peppermint, α-pinene, β-pinene, linalool, nerol, α-terpinene, menthofuran, β-terpinene, Y-terpinene, myrcene, geraniol, geranial, neral, citronellal, menthone, isomenthone, 1,8-cineole, ascaridole, bornneol flavonone, terpinolene, sabinene, camphene, citronellol, cinnamic aldehyde, cinnamic alcohols, cinnamic acids, methyl cinnamate, benzyl cinnamate, cinnamyl acetate, cinnamyl cinnamate (styracin), and combinations of any two or more thereof.

12. A composition according to claim 10 wherein said organic polysulfide is di-t-nonyl polysulfide and said odor-masking compound is selected from the group consisting of vanillin, ethyl vanillin, and combinations thereof.

13. A process comprising combining a major amount of an organic polysulfide and an odor-masking amount of an odor-masking compound wherein said organic polysulfide has the formula of $RS_nR'$ in which R and R' are independently a hydrocarbyl radical having one to about 30 carbon atoms and n is a number of 2 to about 10; and said odor-masking compound is selected from the group consisting of wintergreen, cinnamons, terpenes, sesquiterpenes, vanillins, and combinations of any two or more thereof.

14. A process according to claim 13 wherein said amount is in the range of from 1 to about 10,000 mg per Kg of said organic polysulfide.

15. A process according to claim 13 wherein said amount is in the range of from 50 to 1,000 mg per Kg of said organic polysulfide.

16. A process according to claim 13 wherein said organic polysulfide is selected from the group consisting of di-t-butyl trisulfide, di-t-butyl polysulfide, di-t-nonyl polysulfide, di-t-dodecyl polysulfide, di-t-nonyl trisulfide, di-t-dodecyl trisulfide, and combinations of any two or more thereof.

17. A process according to claim 13 wherein said organic polysulfide is di-t-nonyl polysulfide.

18. A process according to claim 13 wherein said odor-masking compound is selected from the group consisting of wintergreen, vanillin, ethyl vanillin, o-vanillin, vanillic acid, oleoresin vanillin, menthol, piperitone, menthyl acetate, neomenthol, pulegone, spearmint ((−)-carvone), carvyl acetates, commint, scotch mint, peppermint, α-pinene, β-pinene, linalool, nerol, α-terpinene, menthofuran, β-terpinene, Y-terpinene, myrcene, geraniol, geranial, neral, citronellal, menthone, isomenthone, 1,8-cineole, ascaridole, bomneol flavonone, terpinolene, sabinene, camphene, citronellol, cinnamic aldehyde, cinnamic alcohols, cinnamic acids, methyl cinnamate, benzyl cinnamate, cinnamyl acetate, cinnamyl cinnamate (styracin), and combinations of any two or more thereof.

19. A process according to claim 14 wherein said odor-masking compound is selected from the group consisting of vanillin, ethyl vanillin, and combinations thereof.

\* \* \* \* \*